US008955515B2

(12) United States Patent
Rakow et al.

(10) Patent No.: US 8,955,515 B2
(45) Date of Patent: Feb. 17, 2015

(54) PATTERNED CHEMICAL SENSOR HAVING INERT OCCLUDING LAYER

(75) Inventors: Neal A. Rakow, Woodbury, MN (US); Thomas W. Holmquist-Brown, St. Paul, MN (US); Brian L. Linzie, Stillwater, MN (US); John C. Hulteen, Afton, MN (US); Duane D. Fansler, Dresser, WI (US); Richard J. Poirier, White Bear Lake, MN (US); Vivek Bharti, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1007 days.

(21) Appl. No.: 12/604,565

(22) Filed: Oct. 23, 2009

(65) Prior Publication Data

US 2011/0094514 A1    Apr. 28, 2011

(51) Int. Cl.
| | |
|---|---|
| *A62B 19/00* | (2006.01) |
| *A62B 18/02* | (2006.01) |
| *A62B 18/08* | (2006.01) |
| *A62B 23/02* | (2006.01) |
| *G01N 31/22* | (2006.01) |

(52) U.S. Cl.
CPC ............... *A62B 19/00* (2013.01); *A62B 18/088* (2013.01); *G01N 31/229* (2013.01)
USPC ............ 128/206.12; 128/202.22; 128/205.27; 422/86; 422/87

(58) Field of Classification Search
USPC ............ 128/205.23, 205.27–205.29, 206.12, 128/206.17, 206.21, 206.28; 435/807; 422/85, 86, 87
See application file for complete search history.

(56) References Cited

U.S. PATENT DOCUMENTS

| | | | |
|---|---|---|---|
| 1,537,519 A | * | 5/1925 | Yablick .......................... 422/119 |
| 3,966,440 A | | 6/1976 | Roberts |
| 4,154,586 A | | 5/1979 | Jones et al. |
| 4,208,194 A | | 6/1980 | Nelson |
| 4,326,514 A | * | 4/1982 | Eian .......................... 128/202.22 |
| 4,365,627 A | | 12/1982 | Wing |
| 4,468,236 A | | 8/1984 | Bauer |

(Continued)

FOREIGN PATENT DOCUMENTS

| | | |
|---|---|---|
| RU | 2208225 | 7/2003 |
| WO | WO 95/12432 | 5/1995 |

(Continued)

OTHER PUBLICATIONS

Budd et al., *Solution-Processed, Organophilic Membrane Derived From a Polymer of Intrinsic Mocroporosity*, Advanced Materials, 2004, vol. 16, No. 5, pp. 456-459.

(Continued)

*Primary Examiner* — Valerie L Skorupa
(74) *Attorney, Agent, or Firm* — Karl G. Hanson

(57) ABSTRACT

A sensor 40 that detects a chemical such as an organic vapor. The sensor 40 includes a film that has a film body 58 that includes a detection layer 48 and that is responsive to the presence of a chemical by providing a color change. The film also includes an occluding layer 54 that has a first major surface 59 and that is bound to the film body 58 but is inert to the detection layer 48 to preclude the occluding layer 54 and the chemical from causing a color change in the film body 58 in an area 42 normal to the first major surface 59 of the occluding layer 54. A sensor having this construction can provide a distinctly visible image on the sensor, which may be helpful in evaluating the remaining life of a filter cartridge.

21 Claims, 2 Drawing Sheets

(56) References Cited

U.S. PATENT DOCUMENTS

| | | | |
|---|---|---|---|
| 4,530,706 A | | 7/1985 | Jones |
| 4,684,380 A | | 8/1987 | Leichnitz |
| 5,297,544 A | | 3/1994 | May et al. |
| 5,323,774 A | * | 6/1994 | Fehlauer .................. 128/206.12 |
| 5,364,593 A | * | 11/1994 | Mihaylov et al. ............... 422/87 |
| 5,699,188 A | | 12/1997 | Gilbert et al. |
| 5,858,457 A | | 1/1999 | Brinker et al. |
| 5,882,774 A | | 3/1999 | Jonza et al. |
| 6,049,419 A | | 4/2000 | Wheatley et al. |
| 6,284,198 B1 | * | 9/2001 | Kirollos et al. ................. 422/87 |
| 6,497,756 B1 | * | 12/2002 | Curado et al. ............... 96/117.5 |
| 6,573,305 B1 | | 6/2003 | Thunhorst et al. |
| 7,255,832 B2 | | 8/2007 | Lawrence et al. |
| 7,442,237 B1 | * | 10/2008 | Gardner ....................... 96/117.5 |
| 7,449,146 B2 | | 11/2008 | Rakow et al. |
| 7,503,962 B2 | | 3/2009 | Attar |
| 2002/0053637 A1 | * | 5/2002 | Conn et al. .................... 250/281 |
| 2004/0142495 A1 | * | 7/2004 | Hartman et al. ............... 436/518 |
| 2004/0184948 A1 | * | 9/2004 | Rakow et al. ..................... 422/1 |
| 2004/0223876 A1 | | 11/2004 | Kirollos et al. |
| 2005/0123443 A1 | * | 6/2005 | Fujiwara et al. ................ 422/58 |
| 2007/0137491 A1 | | 6/2007 | Attar |
| 2008/0063575 A1 | * | 3/2008 | Rakow et al. .................. 422/119 |
| 2008/0063874 A1 | | 3/2008 | Rakow et al. |
| 2010/0178203 A1 | * | 7/2010 | Kane et al. ...................... 422/56 |

FOREIGN PATENT DOCUMENTS

| | | |
|---|---|---|
| WO | WO 97/01778 | 1/1997 |
| WO | WO 2005/012397 A2 | 2/2005 |
| WO | WO 2005/111588 | 11/2005 |

OTHER PUBLICATIONS

Budd et al., *Polymers of Intrinsic Microporosity (PIMs): Robust, Solution-Processable, Organic Nanoporous Materials*, Chem. Commun., (2004), pp. 230-231.

Budd et al., *Free Volume and Intrinsic Microporosity in Polymers*, J. Mater. Chem., (2005), 15, pp. 1977-1986.

Jia et al., *Synthesis of Microporous Silica Templated by Gelatin*, Chemistry Letters, vol. 33, No. 2, pp. 202-203 (2004).

Kresge et al., *Ordered Mesoporous Molecular Sieves Synthesized by a Liquid-Crystal Template Mechanism*, Nature, vol. 359, pp. 710-712 (1992).

McKeown et al., *Polymers of Intrinsic Microporosity (PIMs): Bridging the Void Between Microporous and Polymeric Materials*, Chem. Eur. J., (2005), 11, No. 9, 2610-2620.

Ogawa et al., *A Simple Sol-Gel Route for the Preparation of Silica-Surfactant Mesostructured Materails*, Chem. Commun., (1996), pp. 1149-1150.

Walheim et al., *Nanophase-Separated Polymer Films as High-Performance Antireflection Coatings*, Science, (1999), vol. 283, pp. 520-522.

Wei et al., *A Non-Surfactant Templating Route to Mesoporous Silica Materials*, Adv. Mater., (1998), 3, No. 4, p. 313.

Krause et al., *Bicontinuous Nanoporous Polymers by Carbon Dioxide Foaming*, Macromolecules, (2001), vol. 34, pp. 8792-8807.

U.S. Appl. No. 12/470,865 to Holmquist-Brown et al., filed May 22, 2009, entitled *Filter Cartridge Having Cover for Masking Service Life Indicator*.

U.S. Appl. No. 12/470,890 to Rakow et al., filed May 22, 2009, entitled *Filter Cartridge having Location-Registered View Window for End-of-Service-Life-Indicator (ESLI)*.

U.S. Appl. No. 12/470,920 to Poirier et al., filed May 22, 2009, entitled *Filter Cartridge Having Cone of Visibility for End-of-Service-Life-Indicator (ESLI)*.

U.S. Appl. No. 61/180,483 to Wendland et al., filed May 22, 2009, entitled *Multilayer Colorimetric Sensors*.

U.S. Appl. No. 61/180,492 to Rakow et al., filed May 22, 2009, entitled *Multilayer Colorimetric Sensor Arrays*.

\* cited by examiner

PATTERNED CHEMICAL SENSOR HAVING INERT OCCLUDING LAYER

The present invention pertains to a sensor that can display a predetermined visible pattern in response to chemical exposure.

BACKGROUND

Sensors are commonly used to detect the presence or absence of a particular chemical. Known sensors have been provided in a variety of forms for achieving this purpose. For example, signs and badges have been developed—see, for example, U.S. Pat. No. 6,284,198 and U.S. patent application Ser. No. 2004/0223876A1—along with filters, filter cartridges, and breathing masks (respirators) that include chemical indicators—see, for example, U.S. Pat. Nos. 5,323,774, 5,297,544, and 4,684,308. One particular chemical sensor that has been developed is a passive end-of-service-life indicator (ESLI) that has a film-like body. Within the film body is a detection layer that detects the presence of a particular chemical. Examples of film-like passive ESLIs are described in U.S. Patent Publications 2008/0063575A1 and 2008/0063874A1 to Rakow et al. ESLIs may be tailored to respond to various organic vapors and reactive gases.

ESLIs have been used in filter cartridges to assist in informing the user of when the cartridge has met the end of its service life—see, for example, U.S. Pat. Nos. 7,442,237, 6,497,756, 5,323,774, 5,297,544, 4,684,380, 4,530,706, 4,365,627, 4,326,514, and 4,154,586. U.S. Patent Application 2007/0137491 and Ser. Nos. 12/470,865, 12/470,890, and 12/470,920 also describe filter cartridges that use end-of-service-life indicators. The ESLIs are disposed adjacent to the housing sidewall so that they can be easily viewed from the exterior. The ESLIs are generally designed to be colorimetric sensors—that is they change color after being exposed to a sufficient amount of contaminant in the filtered air. The color change and sensor placement are tailored to provide indication that coincides with when the filter cartridge service life ends. One particular problem with colorimetric ESLIs is that the wearer needs to memorize the original color to know when a color change has occurred if an original reference color is not available adjacent the ESLI. If the wearer fails to do this, the wearer will not be certain whether the ESLI is displaying the original color or the warning color. Because known ESLIs are not fashioned to provide a warning to the user, which warning does not require the user to memorize or distinguish between the original color and the warning color, safety issues may arise if the wearer fails to notice the color change.

SUMMARY OF THE INVENTION

The present invention provides a new sensor that detects a chemical. The sensor comprises a film that includes a film body that comprises a detection layer and that is responsive to the presence of a chemical by providing a color change. The film also includes an occluding layer that has a first major surface and that is bound to the film body but is inert to the detection layer to preclude the occluding layer and the chemical from causing a color change in the film body in an area normal to the first major surface of the occluding layer.

As indicated above, known ESLIs undergo a complete color change that requires the user to distinguish between the original color and the warning color. The present invention overcomes this need to memorize the different colors by providing an occluding layer that is inert to the detection layer. In addition, since the "old" color and the "new" color are placed side-by-side within the same integral film body, the contrast is precisely arranged and is readily discernible, which allows for a variety of images to be produced. Because the occluding layer is inert to the detection layer, the film body does not produce a noticeable color change in response to the presence of the occluding layer, even though it is bound to it. In addition, because the occluding layer is bound to the film body, the chemical that the sensor is responsive to also cannot communicate with the detection layer to cause a color change in that portion of the sensor. Therefore, certain areas of the sensor are masked off to color change and accordingly retain the original sensor color. Thus, when the sensor does undergo a color change, the masked portions of the sensor retain their original color while the other portions assume the warning color. The invention is able to provide a distinct contrast between the original color and the warning color. The user therefore sees two distinct color regions rather than one particular color or a merger of the two. The invention therefore eliminates a need to memorize the difference between the original color and the warning color, and it provides the ability to create a fine line or clear distinction at two different color regions.

The inert occluding layer that is bound to the film body in accordance with the present invention may be provided in a variety of configurations such that a number of distinctly discernible images can be seen by the user. The ability to bond the inert occluding layer to the film body provides good image resolution since the chemical to-be-detected cannot significantly penetrate between the film body and the occluding layer. The inert occluding layer prevents the detection layer from issuing a false positive in that area of the sensor. Therefore, when the user sees a particular image, they know that the sensor has entered its warning mode. This feature is particularly useful for filter cartridges that have met the end of their service life. Once the warning image has been exhibited by the sensor, the user will know that it is time to replace the filter cartridge.

In one particular embodiment, the sensor may be used on a filter cartridge that has markings to indicate the level of service life remaining. The marking may be provided, for example, at 75, 50, 25, or 10% life remaining. This feature allows the sensor to also serve as a remaining life indicator, or "RLI" on the filter cartridge.

Glossary

As used in this document:

"chemical" means a molecule, atom, ion, free radical, or combination of any of these;

"clean air" means a volume of atmospheric ambient air that has been filtered to remove contaminants;

"color change" means producing a second color or hue, which is noticeably different to the human eye from the first color or hue;

"contaminants" means gases, vapors, and particles (including dusts, mists, and fumes) and/or other substances that generally may not be considered to be gases, vapors, or particles but which may be present in air and harmful to a person;

"detection layer" means a layer of material that exhibits a change in an optical property when exposed to a chemical;

"end-of-service-life-indicator" or "ESLI" means a device that is capable of providing a person with information pertaining to when a filter may no longer be suitable for use due to partial or full exhaustion of the filtering capacity;

"exterior gas space" means the ambient atmospheric gas space into which exhaled gas enters after passing through and beyond the mask body and/or exhalation valve;

"film" means a structure that is much larger in two dimensions than in a third;

"film body" means a combination of layers that are in the form of a film and that are capable of producing a color change in response to the presence of a chemical;

"filter cartridge" means a structure that is primarily designed to house a filter material or filter media and that is adapted for connection to a mask body of a personal respiratory protection device;

"filter material" or "filter media" means a structure or combination of parts or elements adapted to provide clear air;

"housing" means a structure or combination of parts that is fashioned for containing another item;

"inert" means inactive to another thing;

"integral" means that the parts in question are made together at the same time and are not two separate parts subsequently brought together;

"interior gas space" means the space between a mask body and a person's face;

"juxtaposed" or "juxtapositioned" means placed in a general side-by-side relationship but not necessarily in contact with each other;

"mask" (when not referring to a "mask body") means having the ability to restrict the view of an object or covering a portion thereof;

"occluding layer" means a layer that obstructs the passage of a certain chemical(s) through it—that is, from a first major surface to a second major surface of the layer;

"polymer" means a material that contains repeating chemical units, regularly or irregularly arranged;

"remaining life indicator" or "RLI" means a device that is capable of providing a person with information pertaining to a remaining filter capacity;

"sorbent" means a material that is capable of capturing, occluding, or altering a contaminant through absorption, adsorption, chemisorption, decomposition, reaction, catalysis, or other suitable means; and "warning signal" means the viewable indication that tells the viewer that the time to replace the filter cartridge has arrived.

DETAILED DESCRIPTION OF PREFERRED EMBODIMENTS

Figure 1:
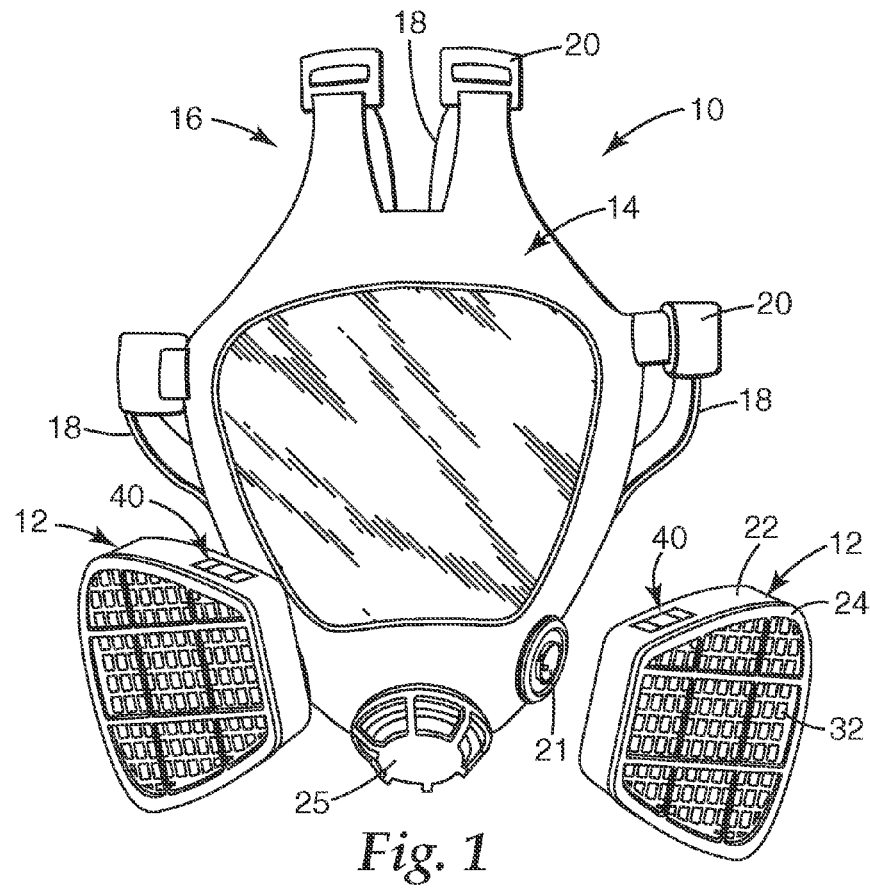
FIG. 1 is a perspective view of a respirator 10 that may use a patterned chemical sensor 40 in the filter cartridge 12.

FIG. 1 shows a respirator 10 that has filter cartridges 12 that can be secured to opposing sides of the mask body 14. The mask body 14 is fashioned to snugly fit on a wearer's face. To this end, the respirator 10 includes a harness 16 for drawing the mask body 14 towards the wearer's face. The harness 16 may include one or more straps 18 for this purpose. The straps 18 may be joined to the mask body 14 and may be adjusted in length through use of buckles 20. The filter cartridges 12 may be attached to the mask body 14 by bayonet attachments 21, threading means, or any other suitable means for securing the cartridge 12 to the mask body 14. The filter cartridges 12 have a housing 22 and a cover 24, which contain a filter media for filtering ambient air that is drawn into the mask interior through the filter cartridge 12. Air that is exhaled by the user passes from the interior gas space to the exterior gas space through the exhalation valve 25.

Figure 2:
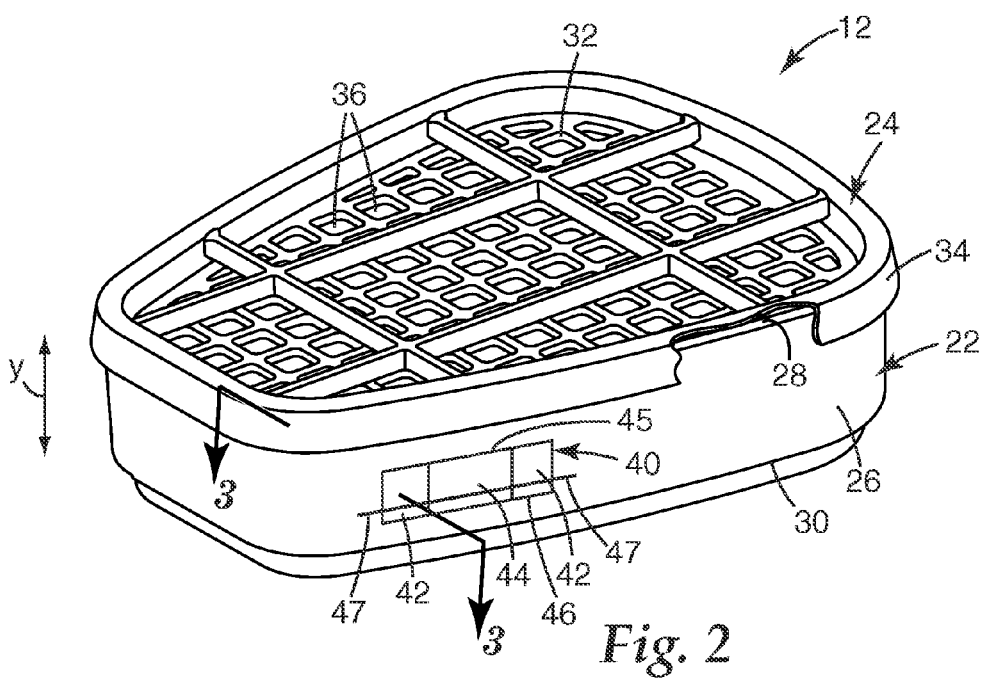
FIG. 2 is a perspective view of a filter cartridge 12 in accordance with the present invention.

FIG. 2 illustrates that the filter cartridges 12 may include a housing 22 that has a sidewall 26 that extends from a first perimeter 28 to a second perimeter 30. The cover 24 may include an air throughput surface 32 and a securement flange 34 located along a periphery of the cover 24. The cover 24 may be secured to the sidewall 26 at the housing perimeter 28. The cover 24 may contain a series of openings 36 in the air throughout surface 32. A sensor 40 may be juxtaposed adjacent to the housing sidewall 26 at its interior surface. The sensor may be designed to detect one or more chemicals, including organic vapors. The sidewall 26 may be transparent in the area of the sensor 40 so that it can be easily viewed by the wearer or another person. Alternatively, the whole sidewall 26 may be transparent so that the sensor 40 and the filter media can be seen therethrough. As illustrated, the sensor 40 includes first and second regions 42, 44, which may take the form of rectangles or stripes. The first region 42 indicates the original color of the sensor, whereas the second region 44 indicates the warning color. Before the filter cartridge 12 is exposed to chemical(s) that the sensor is designed to detect, the whole sensor 40 will display the color 42. Once the filter cartridge has met the end of its service life with respect to one or more of the chemicals that the sensor is intended to detect, region 44 changes to a color different from the original color at 42. The color change may begin at the upstream edge 45 of the region 44 and move progressively across this region 44 toward the second edge 46. One or more marks 47 may be provided on the sidewall 26 to indicate when enough sorptive capacity within the cartridge has been exhausted to require replacement "soon", that is, less than about 60 minutes. The mark may extend across the whole sensor or across the region 44. Alternatively, the marks may be disposed adjacent the sensor. The mark therefore may function similar to an early "empty" signal on a gas gauge in a car. Additional markings could be used to show 25%, 50%, or 75% (or 33 and 66%) consumed. The marking could also be fashioned to note only 10% or 5% of life remaining. As such the sensor functions as a RLI.

The warning mark may be a signal boundary durably or permanently placed across the changing portion of the sensor. This may be achieved through the fabrication of the filter cartridge housing before assembly of the filter cartridge. This fabrication, commonly achieved through injection molding, can result in a visual signal boundary feature such as a fine groove. The signal boundary feature can be produced in molding by several means, such as a ridge, or as a border between areas of differing texture on the surface of the housing. In addition, the signal boundary feature can simply be printed on the side of the housing or onto a label affixed onto the cartridge body adjacent to the sensor. By including this signal boundary feature when fabricating the housing, before the assembly of the filter cartridge, the signal boundary feature can be placed very precisely and repeatably for improved sensor precision and reduced cost of manufacture.

In manufacturing a filter cartridge in connection with the present invention, the filter cartridge housing, filter media, and cover may be manufactured using presently-known or later developed techniques. The filter cartridge housing and cover may be made using injection molding operations. A first scrim may be positioned at the top of a base plenum before introducing the filter material. The filter material may be a filter material that removes gaseous or vapor contaminants and that comprises active particulate that is capable of sorbing one or more undesired contaminants. The sorptive media may include a variety of active particulate such as activated carbon and alumina. U.S. Pat. Nos. 7,309,513 to Brey et al., 5,696,199 to Senkus et al., 5,496,785 to Abler et al., and 5,078,132 to Braun et al., for example, describe various types of active particulate that could be used in filter cartridge of the present invention. The active particulate may be in the form of a packed or bonded bed of such active particulate—see, for example, U.S. Pat. Nos. 5,033,465 to Braun et al., and 6,391,429 to Senkus. The sensor 40 may be placed against the inner surface of the housing sidewall 26 before active particulate introduction. The sensor 40 needs to be properly positioned relative to the y dimension so that the appropriate color change is seen through the housing sidewall 26 when the filter service life has ended. Small deviations in positioning can result in large differences in the response signal. A second scrim may be placed on the upstream surface of the filter material. The upstream scrim may comprise a suitable fibrous medium that helps retain the active particulate in place and provides a low pressure drop thereacross and helps adequately distribute the air that passes through it. Examples of materials that may be used for the scrims include nonwoven polyesters and nonwoven polypropylenes such as spunbond webs. After the filter material and the scrims have been properly positioned in the cartridge housing 22, the cartridge cover 24 may be secured to the housing sidewall 26. The securement may be achieved at the perimeter 28 and flange 34 for example, by mechanical, chemical, or physical means including welding or adhesive bonding, or any other suitable means.

In addition to sorbent active particulate, the filter cartridge also may include one or more layers of filter media fashioned for removing particulates. Fibrous particulate filters may be used upstream or downstream to the active particulate to remove particulate contaminants from the ambient air. A variety of fibrous webs may be suitable for use as particulate filters. These webs typically are nonwoven fibrous structures that can be made from techniques such as air-laid processes, wet-laid processes, hydro-entanglement, spunbond processes, and meltblown processes such as described in Van A. Wente, *Superfine Thermoplastic Fibers*, 48 INDUS. ENGN. CHEM. 1342-46 and in Report No. 4364 of the Naval Research Laboratories, published May 25, 1954, entitled *Manufacture of Super Fine Organic Fibers* by Van A. Wente et al. The fibrous webs can be made using combinations of these techniques and combinations of such fibers. Microfibers, particularly meltblown microfibers, are particularly suitable for use in fibrous webs that are used as filters. As used in this document, "microfiber" means the fiber(s) that have an effective diameter of about 35 micrometers or less. Effective fiber diameter can be calculated using equation number 12 in Davies, C. N., *The Separation of Airborne Dust and Particles*, INST. MECH. ENGN., LONDON PROC. 1B (1952). For filtering applications, the microfibers typically have an effective fiber diameter of less than about 30 micrometers, more typically, about 1 to about 15 micrometers. Fibers made from fibrillated films may also be used—see, for example, U.S. Pat. Nos. RE30,782, RE32,171, 3,998,916 and 4,178,157 to Van Turnout. Staple fibers also may be combined with the microfibers to improve web loft, that is, to reduce its density. Examples of webs that contain staple fibers are disclosed in U.S. Pat. No. 4,118,531 to Hauser.

Figure 3:
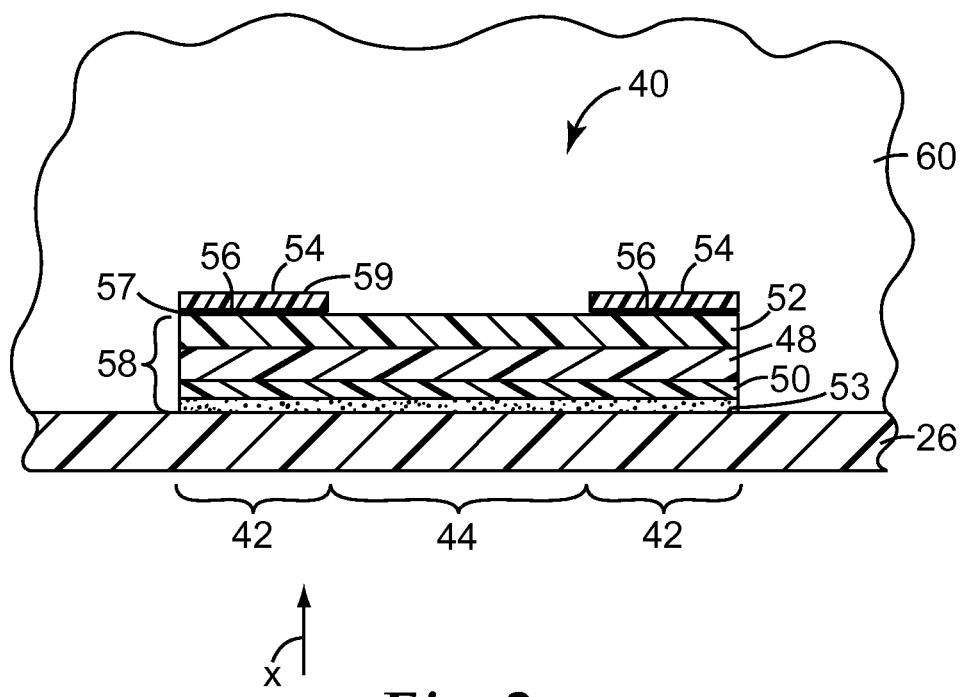
FIG. 3 is a cross-section of the filter cartridge 12 of FIG. 2 taken along lines 3-3.

As shown in FIG. 3, the sensor 40 may comprise a thin film multi-layer construction that can detect a chemical of interest flowing from the gas inlet to the gas outlet of the respirator filter cartridge. Such passive sensors typically contain a porous detection layer 48, a semi-reflective layer 50, and a reflective layer 52. The porous detection layer 48 has an optical thickness (physical thickness does not necessarily change) that will change in the presence of a particular chemical. The semi-reflective layer 50 is viewable from the outside of the cartridge and is generally not permeated by the vapor. The reflective layer 52 is generally permeable to the chemical and is in sufficient proximity to the filter media such that the chemical (such as a vapor) can pass through the reflective layer into the detection layer 48 and can change the detection layer optical thickness sufficiently to cause a visibly discernible change in the indicator appearance as viewed through the semi-reflective layer 50. An adhesive 53 may be used to secure the sensor 40 to an inner surface of the housing sidewall 26.

An occluding layer 54 may be disposed on opposing sides of the second region 44, which region 44 changes color in response to exposure to one or more chemicals. The occluding layer 54 may be bonded to the reflective layer 52 at an interface 56. The interface 56 may be an adhesive layer that is inert to the detection layer 48. Alternatively, occluding layer 54 itself may be an adhesive layer that is inert to the detection layer 48. When an occluding layer 54 is bonded to the reflective layers 52, the detection layer 48 does not undergo a substantial optical change in regions 42. Without an inert occluding layer 54 bonded to the film body 58, the film body 58 would normally produce a color change that is visible to a person viewing the film body normal to the outer major surface of the sensor 40. Thus, when the film is viewed in the direction x normal to the first major surface 59 of the occluding layer 54, no visible color change is seen in regions 42 of the sensor. The first region 42 therefore does not change color, whereas the second region 44 produces a noticeable color change that is visible to a user viewing the sensor 40 in the direction x. Although regions 42 and 44 display different colors or hues, the regions are integral to each other in the film body 58. When a chemical is passing through the filter media 60, a progressive color change may be noticed by the user moving from the upstream side of the filter media towards the downstream side.

A sensor that is used in connection with the present invention may be rigid or flexible. It can be secured to the housing sidewall 26 by various means such as adhesive, physical, packing techniques, or mechanical engagement. Flexible indicators desirably are sufficiently bendable without fracturing so that they can be made using one or more roll processing steps.

Sensors that may be used in connection with the present invention preferably are passive sensors that absorb or adsorb gaseous vapors that are desired to be filtered from the air. The sensor may be essentially any known or later developed device (passive or active) that is capable of providing the proper indication to the respirator wearer that the filter has met the end of its useful life. Examples of passive sensors have been described in U.S. Patent Publications 2008/0063575A1 and 2008/0063874A1 to Rakow et al.—see also U.S. Pat. No. 7,449,146B2 to Rakow et al. and U.S. Patent applications 61/180,483 to Wendland et al. and 61/180,492 to Rakow et al. Sensors that may be employed include ESLIs that respond to organic vapors, reactive gases such as acidic (for example, $SO_2$, $Cl_2$, HCl, $ClO_2$, HCN, HF, $H_2S$ and oxides of nitrogen) and basic gases (for example, ammonia, methylamine), and cyanogen chloride and formaldehyde.

The sensor may include an optional substrate such as glass or a flexible plastic film that may be handled in one or more roll processing steps. The substrate desirably has sufficiently low vapor permeability so that the chemical(s) of interest will not be transmitted into or out of the detection layer. The adhesive attaching the sensor to the sidewall should be inert so that it does not contaminate the detection layer. Also, a porous substrate may be placed between the reflective layer and the sorbent media. Chemicals of interest could be allowed to pass from the sorbent media through the permeable substrate and reflective layer and thence into the detection layer. The overall thickness of the sensor (excluding a substrate) may be about 0.5 to 2 micrometers (μm).

The semi-reflective and reflective layers each may be made from a variety of materials that provide diffuse or preferably specular light reflection and that can cooperate when appropriately spaced apart to provide a readily visibly perceptible indicator appearance change. Suitable semi-reflective and reflective layer materials include metals such as aluminum, chromium, gold, nickel, silicon, silver, palladium, platinum, titanium and alloys containing such metals; metal oxides such as chrome oxide, titanium oxide and aluminum oxide; and the multilayer optical films (including birefringent multilayer optical films) described in U.S. Pat. Nos. 5,699,188 (Gilbert et al.), 5,882,774 (Jonza et al.) and 6,049,419 (Wheatley et al.), and PCT Published Application No. WO 97/01778 (Ouderkirk et al.). The semi-reflective and reflective layers may be the same or different. Metal nanoparticle coatings (e.g., metal nanoparticle inks) may be used to form the reflective layer, as described in U.S. patent application Ser. No. 11/530,619 entitled Permeable Nanoparticle Reflector.

The semi-reflective layer is generally less reflective than the reflective layer and transmits some incident light. The semi-reflective layer may, for example, have a physical thickness of about 2 to about 50 nanometers (nm), light transmission at 500 nm of about 10 to about 80%, and reflectance at 500 nm of about 80 to about 20%. The semi-reflective layer may itself be impermeable to a chemical (and if so desirably is continuous) and optionally coated on or otherwise adjacent to a suitable substrate. The semi-reflective layer also may be permeable to a chemical (and if so may, for example, be discontinuous or semi-continuous) and coated on or otherwise adjacent to a suitably vapor-impermeable substrate. The face of the semi-reflective layer adjacent the detection layer desirably is flat to within about ±20 nm.

The reflective layer may, for example, have a physical thickness of about 1 to about 500 nm, light transmission at 500 nm of about 0 to about 80%, and reflectance at 500 nm of about 100 to about 20%. The reflective layer preferably is porous, patterned, discontinuous, semi-continuous, or otherwise sufficiently permeable so that vapor can pass from the sorbent media through the reflective layer into the detection layer.

The detection layer mixture may be homogeneous or heterogeneous, and may, for example, be made from a mixture of inorganic components, a mixture of organic components, or a mixture of inorganic and organic components. Detection layers made from a mixture of components may provide improved detection of analyte groups. The detection layer desirably has a range of pore sizes or a surface area selected to provide sorption characteristics like those of the sorbent media. Suitable porosity can be obtained using porous materials such as foams made from high internal phase emulsions, such as those described in U.S. Pat. No. 6,573,305 B1 (Thunhorst et al.). Porosity may also be obtained via carbon dioxide foaming to create a microporous material (see "Macromolecules", 2001, vol. 34, pp. 8792-8801), or by nanophase separation of polymer blends (see "Science", 1999, vol. 283, p. 520). In general, the pore diameters preferably are smaller than the peak wavelength of the desired indicator coloration. Nano-sized pores are preferred, for example, with average pore sizes of about 0.5 to about 20 nm, 0.5 to about 10 nm, or 0.5 to about 5 nm.

Representative inorganic detection layer materials include porous silica, metal oxides, metal nitrides, metal oxynitrides and other inorganic materials that can be formed into transparent and porous layers of appropriate thickness for producing color or a colorimetric change by optical interference. For example, the inorganic detection layer materials may be silicon oxides, silicon nitrides, silicon oxynitrides, aluminum oxides, titanium oxides, titanium nitride, titanium oxynitride, tin oxides, zirconium oxides, zeolites or combinations thereof. Porous silica is an especially desirable inorganic detection layer material due to its robustness and compatibility with wet etching treatments.

Representative porous silica materials are described in Ogawa et al., *Chem. Commun.* pp. 1149-1150 (1996), in Kresge et al., *Nature*, Vol. 359, pp. 710-712 (1992), in Jia et al., *Chemistry Letters*, Vol. 33(2), pp. 202-203 (2004) and in U.S. Pat. No. 5,858,457 (Brinker et al.). A variety of organic molecules also be employed as organic templates. For example, sugars such as glucose and mannose may be used as organic templates to generate porous silicates, see Wei et al, *Adv. Mater.* 1998, Vol. 10, p. 313 (1998).

Representative organic detection layer materials include polymers, copolymers (including block copolymers) and mixtures thereof prepared or preparable from classes of monomers including hydrophobic acrylates and methacrylates, difunctional monomers, vinyl monomers, hydrocarbon monomers (olefins), silane monomers, fluorinated monomers, hydroxylated monomers, acrylamides, anhydrides, aldehyde-functionalized monomers, amine- or amine salt-functionalized monomers, acid-functionalized monomers, epoxide-functionalized monomers and mixtures or combinations thereof U.S. Patent Application Publication No. US 2004/0184948 A1 contains an extensive list of such monomers. The above-mentioned polymers having intrinsic microporosity (PIMs) provide particularly desirable detection layers. PIMs typically are non-network polymers that form microporous solids. Due to their typically highly rigid and contorted molecular structures, PIMs are unable to fill space efficiently, thus providing the disclosed microporous structure. Suitable PIMs include, but are not limited to, polymers disclosed in "Polymers of intrinsic microporosity (PIMs): robust, solution-processable, organic microporous materials," Budd et al., *Chem. Commun.*, 2004, pp. 230-231. Additional PIMs are disclosed in Budd et al., *J. Mater. Chem.*, 2005, 15, pp. 1977-1986, in McKeown et al., *Chem. Eur. J.* 2005, 11, No. 9, 2610-2620 and in Published PCT application No. WO 2005/012397 A2 (McKeown et al.).

The occluding layer for the chemical sensor films of the invention preferably is easily patterned, has low or no chemical permeability, and contains no, or minimal amounts, of organic small molecule contaminants that can leach into the sensor and cause undesired color change adjacent to the masked areas—that is, normal to the major surfaces of the occluding layer. The regions masked by the occluding layers are ideally visually inconspicuous relative to the unmasked areas before exposure of the sensor to the analyte.

In one embodiment, pressure-sensitive adhesives may be used as occluding layers. Polyisobutylene (PIB) adhesives are useful materials for these layers based especially on their high purity. The polymers are prepared from isobutylene monomer, so that any residuals in their preparation are gases, not vapors that could be sorbed by the film body. Polyisobutylene materials are commercially available from several manufacturers. Homopolymers are commercially available, for example, under the trade designation OPPANOL (e.g., OPPANOL B15, B30, B50, B100, B150, and B200) from BASF Corp. (Florham Park, N.J.). These polymers often have a weight average molecular weight of about 40,000 to 4,000,000 grams/mole. Still other exemplary homopolymers are commercially available from United Chemical Products (UCP) of St. Petersburg, Russia in a wide range of molecular weights. For example, homopolymers commercially available from UCP under the trade designation SDG have a viscosity average molecular weight in the range of about 35,000 to 65,000 grams/mole. Homopolymers commercially available from UCP under the trade designation EFROLEN have a viscosity average molecular weight in the range of about 480,000 to about 4,000,000 grams/mole. Homopolymers commercially available from UCP under the trade designation JHY have a viscosity average molecular weight in the range of about 3,000 to about 55,000 grams/mole. These homopolymers typically do not have reactive double bonds.

Other suitable polyisobutylene homopolymers are commercially available under the trade designation GLISSOPAL (e.g., GLISSOPAL 1000, 1300, and 2300) from BASF Corp. (Florham Park, N.J.). These polyisobutylene materials usually have terminal double bonds and are considered to be reactive polyisobutylene materials. These polymers often have a number average molecular weight in the range of about 500 to about 2,300 grams/mole. The ratio of the weight average molecular weight to the number average molecular weight is typically in the range of about 1.6 to 2.0.

Polyisobutylene copolymers may be prepared by polymerizing isobutylene in the presence of a small amount of another monomer such as, for example, styrene, isoprene, butene, or butadiene. These copolymers are typically prepared from a monomer mixture that includes at least 70 weight percent, at least 75 weight percent, at least 80 weight percent, at least 85 weight percent, at least 90 weight percent, or at least 95 weight percent isobutylene based on the weight of monomers in the monomer mixture. Suitable isobutylene/isoprene copolymers are commercially available under the trade designation EXXON BUTYL (e.g., EXXON BUTYL 065, 068, and 268) from Exxon Mobil Corp. These materials have an unsaturation of about 1.05 to about 2.30 mole percent. Other exemplary isobutylene/isoprene copolymers are commercially available from United Chemical Products (St. Petersburg, Russia) such as BK-1675N with an unsaturation of about 1.7 mole percent. Still other exemplary isobutylene/isoprene copolymers are commercially available from LANXESS (Sarnia, Ontario, Canada) such as LANXESS BUTYL 301 with an unsaturation of about 1.85 mole percent, LANXESS BUTYL 101-3 with an unsaturation of about 1.75 mole percent, and LANXESS BUTYL 402 with an unsaturation of about 2.25 weight percent. Suitable isobutylene/styrene block copolymers are commercially available under the trade designation SIBSTAR from Kaneka (Osaka, Japan). These materials are available as both diblocks and triblocks with the styrene content varying from about 15 to 30 weight percent based on the weight of the copolymer. Polyolefin elastomers such as ethylene-octene block copolymers (commercially available from Dow Chemical under the trade name INFUSE) may also be used for sensor masking. Ethylene-octene copolymers, under the trade name Engage (Dow Chemical, Midland, Mich.) also may be used for masking the sensor. Other polyolefins that meet the Dahlquist Criterion for tack, including polymers, blends, or copolymers synthesized from monounsaturated hydrocarbons from C2 to C12, may be used, especially polyhexene and polyoctene. Cyclic polyolefins are also useful for masking the sensor, as are masticated or tackified rubbers.

Other pressure-sensitive adhesives useful for film body masking include acrylic-based adhesives. Many acrylic based adhesives have high levels of residual solvent and/or monomer that will migrate into the sensor, resulting in an undesired color change. If these residuals, however, are driven out of the adhesive before attaching to the sensor, acrylic adhesives can act as an excellent occluding layer. Examples of acrylic-based PSA's that do not cause an undesirable color change to the sensor color are 3M™ Very Low Outgassing adhesives, found for example in Linered Polyester Tape 6690 and Very Low Outgassing High Shear Polyester Tape 8439, and 3M™ Optically Clear Adhesive 8172.

In one embodiment, the pressure-sensitive adhesives are applied to the film body in the form of pressure-sensitive tapes, wherein they are coated on a liner film, cut into pieces, and then adhered to the sensor film. In this implementation, the liner often provides an additional barrier to permeation of vapors into the sensor; hence, the liner is typically left attached to the adhesive after application. In a similar fashion, a backing may be used, thus providing a masking tape. The tape or adhesive can be between two liners with differential peel, a backing-liner combination, or a single backing with a low-adhesion backsize. Liners can be chosen according to their release chemistry and release value, measured in ounces per inch (oz/in) or Newtons per decimeter (N/dM). Ideally one will avoid release chemistries that may contaminate the sensor or transfer, even in low amounts, to the adhesive, thus changing the peel value to the sensor film. The invention also provides adhesive masking articles such as tapes and the like comprising a layer of the foregoing pressure sensitive adhesive disposed on a support or backing. The support may be a release substrate or liner to provide a so-called transfer tape, wherein the exposed adhesive may be placed in contact with a substrate or surface and the release liner may thereafter be stripped away from the adhesive to expose another portion of the adhesive for bonding to another substrate or surface. The adhesive article may be provided as a tape or an adhesive sheet that can be prepared by any of a variety of known methods such as by extruding, coating, or spraying the adhesive composition onto a backing layer. The pressure sensitive adhesive tape or sheet can be laminated onto a surface or the film body. The tape or sheet can also be die-cut into any desired shape. Examples of suitable substrates include release liners (e.g., silicone release liners) and tape backings (which may be primed or unprimed paper or plastic).

Examples of liners include the T-series of liners from CP Films, St. Louis, Mo. Suitable materials for backings include polyolefins, polystyrene, polyester, polyvinyl chloride, polyvinyl alcohol, polyurethane, poly(vinylidene fluoride), cellulose and cellulose derivates.

Hot melt, solution-free, adhesives can be applied as masking materials. These materials are applied at elevated temperature (typically at least 150 degrees Fahrenheit) onto the sensor film and then allowed to cool to leave a solid occluding layer. Preferred hot melt adhesives contain no small-molecule coadditives that may contaminate the sensor. Examples include Scotch Weld™ Hot Melt adhesives from 3M Company, such as Scotch Weld Adhesive 3779 and 3789. The adhesives are 100% solids thermoplastic and thermosetting resins that become fluid when heated and cool and harden in seconds. These adhesives can be applied to the film body using a hot melt glue gun, such as a Stanley Bostitch SBGR-30K glue gun, or hotmelt applicators from the 3M Scotch Weld™ family of products. The material is allowed to cool to room temperature before the sensor is used.

Polymeric materials can also be used as occluding layers to mask regions of the film body. In one embodiment, water-soluble polymers are used for masking the film body. Examples of waterborne polymer useful for masking include, but are not limited to: poly(vinyl alcohol), ethyl cellulose, hydroxyethylcellulose, and poly(ethylene glycol). Polymers and copolymers prepared from the following classes of monomers may also be used: vinyl alcohol, vinyl phenol, ethylene glycol, ethylene oxide. Typically these polymers would be prepared in an aqueous solution and then applied to the film body to give a conformal coating to mask the film body in the desired regions. Application can be done through solution coating techniques, including but not limited to swabbing, spincoating, spraycoating, dipcoating, gravure coating, die coating, ink jet printing, and screen printing. Polymeric solutions may also be spotted using a syringe or pipet onto the film body. The coated film bodies are dried, either at ambient or elevated temperature before use.

Another representative class of polymeric occluding layer includes epoxies. Typically, epoxy materials are either UV or thermally cured. The requirements for this process are that the base epoxy polymer is large enough on a molecular level to not leach into the film body, the process is solventless, and the epoxy be cured quickly after being applied to the film body. The epoxy could be applied under similar applications to those described above with a cure cycle post application. An example of such an epoxy would be Momentive™ UV9500, a solventless, photocurable epoxysilicone polymer.

Waxes or resins, for example, an organic material used in thermal printing, may be employed for film body masking. These include but are not limited to waxes and resins used in thermal printing processes. Commercial examples include ColorStix materials from Tektronix, Inc., and Solid Ink materials from Xerox Inc.

Inorganic materials also may be used for the occluding layer. These include metals, including but not limited to aluminum, chromium, gold, nickel, silicon, silver, platinum, and palladium. Metallic and semi-metallic oxides, such as oxides, nitrides, carbides, phosphides, and sulfides of silicon, titanium, and chromium may also be employed, or mixtures of these materials. These can be applied through vacuum coating techniques, such as sputtering, evaporative coating, chemical vapor deposition, or plasma-deposition, to selected areas of the film body. Masks may be utilized to cover the source or target in these coating methods so as to create desired deposition patterns on the sensor substrate. For example, a mask that contains a series of slots will produce an occluding layer that comprises lines on the sensor substrate. Solution coating techniques, including but not limited to swabbing, spincoating, spraycoating, dipcoating, gravure coating, die coating, ink jet printing, and screen printing may also be used to deposit inorganic materials or their precursors. For example, inorganic sol-gel processing may be used to deposit inorganic precursors that react after depositions to create inorganic oxides or other inorganic materials.

The occluding layer as described above may be applied to sensors to produce a variety of different visual patterns useful for chemical indication. Patterns revealed upon exposure to chemical analytes may include shapes, letters, logos, indications of remaining filtering capacity, messages, instructions, or other indications to the user.

The sensor may include additional layers or elements if desired. For example, a porous layer of sorbent-loaded composite (e.g., a web of activated carbon particles ensconced in a matrix of fibrillated PTFE such as is described in the above-mentioned U.S. Pat. No. 4,208,194) may be placed between the reflective layer and the sorbent media, to homogenize vapors permeating into the indicator or otherwise moderate the indicator response to conditions in the sorbent media. When a portion of the sensor changes to the color or hue that indicates that the filter cartridge should be replaced, the change in such appearance reflects a specified level of sorbent depletion that mandates replacement of the filter cartridge. In other words, the filter cartridge manufacturer may adjust the selection of the particular sensor such that the particular level of sorbent depletion can be achieved. The selection of the sorbent depletion level may depend on a variety of factors, including providing a sufficient buffer so that the sorbent is not 100% depleted when the filter cartridge is identified as being needed to be replaced. The level of sorbent depletion may, for example, be identified to provide one to three hours of additional use so that the wearer has adequate time to notice that the sensor has undergone the color change indicating satisfaction of the response signal or need for cartridge replacement.

Although the present invention has been illustrated using a full-face respirator mask that covers the wearer's nose, mouth, and eyes, the present invention also may be used in conjunction with half-mask that cover only the nose and mouth of a wearer. Further, the filter cartridges that are used in connection with the present invention may be permanently or removably attached to the mask body. The harness also may come in a variety of configurations and may include additional parts such as a crown member to support the respirator on a wearer's head. Accordingly, a variety of embodiments are contemplated by the invention when providing sensors and respiratory masks that have sensors disposed on the filter cartridge.

EXAMPLES

The invention is further illustrated in the following illustrative example, in which all parts and percentages are by weight unless otherwise indicated. The abbreviations shown below in Table 1 are used in the example description:

TABLE 1

| ABBREVIATION | DESCRIPTION |
|---|---|
| BC | bis-catechol; 5,5',6,6'-tetrahydroxy-3,3,3',3'-tetramethyl-1,1'-spirobisindane |
| FA | fluorinated arene; tetrafluoroterephthalonitrile |
| DMF | N,N-dimethylformamide |
| THF | Tetrahydrofuran |

Example 1

An example of the invention was made by constructing four layers of material into a sensor film. Layers of the sensor film consisted of: (1) a semi-reflective layer; (2) a porous detection layer; (3) a reflective layer; and (4) an occluding layer.

Construction of the sensor film began by creating the semi-reflective layer, which was made by coating nickel onto one surface of a polyethylene terephthalate (PET) film (Melinex ST505 clear PET, [Dupont Teijin Films], [Hopewell, Va.]). Nickel was applied to the PET using thermal evaporation under vacuum (base pressure of $10^{-5}$ torr). Two Temescal Simba 2 electron beam sources (Edwards Corporation, Tewksbury, Mass.) were used to heat the nickel in graphite crucibles; nickel was deposited until a target optical transparency of 27% was reached, corresponding to a thickness of approximately 10 nm.

The second layer of the sensor film, which was applied to the Ni coated side of the semi-reflective layer, was a polymer layer of intrinsic microporosity (PIM). PIM material was prepared from monomers, as is generally prescribed in the procedure reported by Budd et al. in Advanced Materials, 2004, Vol. 16, No. 5, pp. 456-459. The PIM material was formed by mixing 9.0 grams of BC with 5.28 g of FA, 18.0 g potassium carbonate, and 120 milliliters of DMF. The mixture was then reacted at 70° C. for 24 hours. The resulting polymer was then dissolved in THF, precipitated three times from methanol, and dried under vacuum at room temperature. Following this procedure, a solid yellow polymer product was obtained having a molecular weight (Mw) of 61,800. The PIM material was then solution-coated using slotted die deposition onto the Ni surface of the semi-reflective layer using a 4% solution of the material in chlorobenzene. After drying at 121° C. for 3 minutes, the resulting PIM coating had a thickness of approximately 650 micrometers (μm).

The third layer of the sensor film, the reflective layer, was a layer of nanosilver formed onto the PIM material layer. Nanosilver was solution-coated onto the PIM layer using a 1:1.5 solution of a nanosilver suspension (DGP-40LT-15C, Advanced Nanoproducts, Chungcheongbuk-do, Korea) and 1-methoxy-2-propanol. The solution was coated using slotted die deposition onto the PIM material layer and subsequently heated at 130° C. for 12 hours to sinter the silver particles, resulting in a reflective layer of approximately 150 μm thicknesses.

The fourth and final layer of the film sensor, the occluding layer, was attached to the nanosilver reflective layer to create a pattern of occluded and non-occluded areas of desired configuration. Blends of Polyisobutylene (PIB) adhesives (Oppanol, types B80 and B15, BASF, Florham Park, N.J.) were used as the occluding material and attached to the exposed reflective layer with the aid of a film release liner (T-30, CP Films, St. Louis, Mo.). Oppanol type adhesives were selected for the application due to their high purity and low organic vapor residuals. The adhesive layer was prepared by coating a 4:1 blend of B80 and B15 adhesives respectively in an 11.1% solids solution in toluene. The solution was coated onto the release liner and allowed to dry at 70° C. for 30 min, resulting in an adhesive thickness of 0.025 mm. The adhesive was then applied to the reflective layer in the desired pattern with one of the release liners intact, so forming the occluding layer.

Function of the sensor film was evaluated by attaching a piece of the film to the inner surface of a clear-walled sealed chamber and flushing the chamber with a challenge of 500 parts per million (ppm) octane in air, delivered at atmospheric pressure. Color of the sensor film was then observed after equilibrium was reached between the non-occluded portion of the sensor film and the challenge. For the evaluation, a 1.5 cm×1.0 cm piece of sensor film, with a 3 mm wide×10 mm long non-occluded rectangular strip pattern in the center, was adhered to the inner wall of the 105 cubic centimeter volume sealed chamber using transfer adhesive (8172, 3M Company, St. Paul, Minn.). The length of the non-occluded pattern was oriented parallel to the shorter dimension of the film piece, with the transfer adhesive having been applied to the semi-reflective layer of the film sensor for attachment to the chamber wall. With the sensor film piece affixed to the chamber wall, the challenge was introduced at a volumetric rate of 32.0 liters per minute. Temperature of the sensor film and challenge were approximately 25° C. After providing sufficient time for the non-occluded strip of the sensor film to equilibrate with the challenge, the color of the occluded and non-occluded portion of the film sensor was observed through the clear wall of the chamber. It was noted that the non-occluded strip had a distinctive red color while the occluded section retained the original green appearance of the sensor film. Color resolution, or fidelity, between red and green sections of the sensor film were sharp and distinctive.

Comparative Example 1

Mask not Bonded

A sensor was prepared and attached to a clear chamber wall as described in Example 1 except that the sensor mask was a PET film attached using Scotch™ tape. An 8 mm diameter dermal punch (Miltex, York, Pa.) was used to place a hole into the center of a 2.0 cm×1.5 cm piece of polyethylene terephthalate (PET) film (Melinex ST505 clear PET, Dupont Teijin Films, Hopewell, Va.). The PET film was placed over the sensor film within the chamber so that the center hole covered the middle section of the reflective layer of the sensor. The PET film was attached to the walls of the chamber using pressure sensitive adhesive tape (Magic™ Tape 810, 3M, St. Paul, Minn.). Function of the masked sensor film was evaluated by flushing the chamber with a challenge of 500 parts per million (ppm) octane in air, delivered at atmospheric pressure. With the sensor film piece affixed to the chamber wall, the challenge was introduced at a volumetric rate of 32.0 liters per minute. Temperatures of the sensor film and challenge vapor were approximately 25° C. After providing sufficient time for the sensor film to equilibrate with the challenge, the color difference between the occluded and non-occluded portion of the film sensor was observed through the clear wall of the chamber. It was noted that the both the non-occluded sensor section and a majority of the occluded section had a distinctive red color while a small fraction of the occluded section retained the original green appearance of the sensor film. Color resolution, or fidelity, between red and green sections of the sensor film was poor, so that no definitive shape or pattern could be deciphered.

Comparative Example 2

Mask not Inert

A 1.5 cm×1.0 cm piece of sensor film was prepared as described in Example 1. Half of the sensor was masked by applying a 0.75 cm×1.0 cm piece of pressure sensitive adhesive tape (Magic™ Tape 810, 3M, St. Paul, Minn.) to the reflective layer of the sensor. Upon standing for 12 hours at approximately 25° C., the masked section of sensor took on a distinctive red color while the unmasked section of the sensor remained green, demonstrating that the tape mask was not inert relative to the PIM-based detection layer used above. This evaluation demonstrated the contaminating effect of the 810 tape, producing a false positive of detection, for detection layers sensitive to volatile organic residuals that can be present in certain adhesive.

This invention may take on various modifications and alterations without departing from its spirit and scope. Accordingly, this invention is not limited to the above-described but is to be controlled by the limitations set forth in the following claims and any equivalents thereof.

This invention also may be suitably practiced in the absence of any element not specifically disclosed herein.

All patents and patent applications cited above, including those in the Background section, are incorporated by reference into this document in total. To the extent there is a conflict or discrepancy between the disclosure in such incorporated document and the above specification, the above specification will control.

What is claimed is:

1. A sensor that detects a chemical, the sensor comprising:
a film that includes a film body that is responsive to the presence of a chemical by providing a color change and that comprises:
   (a) a detection layer;
   (b) an occluding layer that has a first major surface and that is bound to the film body but is inert to the detection layer to preclude the occluding layer and the chemical from causing a color change in the film body in an area normal to the first major surface of the occluding layer;
   (c) a reflective layer located between the occluding layer and the detection layer; and
   (d) a semi-reflective layer located on a side of the detection layer opposite the reflective layer;
   wherein the semi-reflective layer is less reflective than the reflective layer.

2. The sensor of claim 1, wherein the occluding layer comprises an adhesive.

3. The sensor of claim 2, wherein the occluding layer comprises a pressure-sensitive adhesive (PSA).

4. The sensor of claim 3, wherein the occluding layer is a PSA, and wherein the sensor detects organic vapors.

5. The sensor of claim 4, wherein the PSA comprises polyisobutylene, a polyisobutylene copolymer, or an acrylic polymer, or combination thereof.

6. The sensor of claim 3, wherein the PSA comprises polyisobutylene, a polyisobutylene copolymer, an acrylic, or combination thereof.

7. The sensor of claim 2, wherein the occluding layer comprises a hot-melt adhesive.

8. The sensor of claim 1, wherein the occluding layer comprises a water-soluble polymer or copolymer.

9. The sensor of claim 1, wherein the occluding layer comprises an epoxy.

10. The sensor of claim 1, wherein the occluding layer comprises a wax.

11. The sensor of claim 1, wherein the occluding layer comprises a resin.

12. The sensor of claim 1 being an end-of-service-life indicator.

13. The sensor of claim 1 being a remaining-life-indicator.

14. A filter cartridge that comprises a housing, filter media disposed within the housing, and the sensor of claim 1 visible through a sidewall of the housing.

15. The filter cartridge of claim 14, wherein the filter cartridge comprises one or more markings that indicate filter cartridge remaining life.

16. The filter cartridge of claim 15, wherein the marking(s) are molded into the sidewall of the cartridge housing.

17. A respirator that comprises a mask body and one or more filter cartridges of claim 14.

18. A filter cartridge that comprises:
   (a) the sensor of claim 1;
   (b) a housing that comprises a sidewall;
   (c) a cover that is secured to a first perimeter of the sidewall; and
   (d) filter media that is disposed within the housing;
   wherein the sensor is juxtapositioned against an inner surface of the housing sidewall, the housing sidewall being transparent at least in an area where the sensor is located, the housing sidewall including one or more markings to convey remaining life of the cartridge to the user.

19. The filter cartridge of claim 18, wherein the marking(s) are molded into the housing sidewall.

20. A respirator that comprises a mask body, a harness that is secured to the mask body, and one or more cartridges of claim 18 attachable to the mask body.

21. The sensor of claim 1, further comprising a substrate onto which the film body is disposed, the film body being oriented on the substrate such that the semi-reflective layer is located between the substrate and the detection layer.

* * * * *